United States Patent [19]
Connery et al.

[11] Patent Number: 4,851,104
[45] Date of Patent: Jul. 25, 1989

[54] INSTRUMENT FOR POTENTIOMETRIC ELECTROCHEMICAL MEASUREMENTS

[75] Inventors: James G. Connery, Ambler; Earl W. Shaffer, Jr., Lansdale, both of Pa.

[73] Assignee: General Signal Corporation, Stamford, Conn.

[21] Appl. No.: 220,922

[22] Filed: Jul. 18, 1988

Related U.S. Application Data

[63] Continuation of Ser. No. 20,056, Feb. 27, 1987, abandoned.

[51] Int. Cl.$^4$ ............................................. G01N 27/26
[52] U.S. Cl. .................................... 204/406; 204/412; 204/416
[58] Field of Search ............... 204/406, 412, 416, 417, 204/418, 419, 420

[56] References Cited

U.S. PATENT DOCUMENTS

| | | | |
|---|---|---|---|
| 3,862,895 | 1/1975 | King et al. | 204/412 |
| 4,189,367 | 2/1980 | Connery et al. | 204/401 |
| 4,385,274 | 5/1983 | Shimada et al. | 204/416 |
| 4,426,621 | 1/1984 | Galwey et al. | 204/412 |
| 4,498,039 | 2/1985 | Galwey et al. | 204/412 |
| 4,505,799 | 3/1985 | Baxter | 204/416 |
| 4,560,840 | 2/1985 | Galwey et al. | 204/406 |

*Primary Examiner*—John F. Niebling
*Assistant Examiner*—Steven P. Marquis
*Attorney, Agent, or Firm*—Harold Huberfeld; William G. Miller, Jr.

[57] ABSTRACT

There is provided a system for measuring a selected ion in a solution so as to avoid noise pickup from AC parasitic currents and measurement offset from DC parasitic currents, such as are frequently found in pH measurements on low conductivity grounded solutions like high purity water. The system in one form has an operational amplifier with an ion selective electrode connected to its inverting input, a counter electrode connected to its output, and circuit common connected to the non-inverting input, so that the potential of the ion selective electrode is continuously driven to circuit common. The reference electrode of the system is connected to a high impedance measuring circuit for measuring the voltage level of that electrode with reference to circuit common as a measure of the concentration of the selected ion in the solution.

9 Claims, 2 Drawing Sheets

INSTRUMENT FOR POTENTIOMETRIC ELECTROCHEMICAL MEASUREMENTS

This application is a continuation of application Ser. No. 020,056 filed on Feb. 27, 1987 now abandonded.

BACKGROUND OF THE INVENTION

This invention relates to apparatus for potentiometric electrochemical measurements employing ion selective probe systems such as glass pH electrode systems or other ion-selective electrode systems and ISFET pH devices. It is particularly useful in making pH measurements with these probe systems in solutions of low electrolytic conductivity, such as high purity water.

A typical pH measuring system, as found in the prior art, is shown in U.S. Pat. No. 4,189,367, issued to the present inventors on Feb. 19, 1980. That system utilizes an operational amplifier to drive the reference electrode through the low impedence output of the amplifier to maintain the pH electrode, connected to the amplifiers high input impedance summing junction, at signal common voltage. Such a measurement approach is entirely adequate for solutions with an electrolytic conductivity greater than 1 micromho. However, when such systems are used for pH measurements of earth grounded solutions of high purity water (less than 0.1 micromho), such as are found in electric power plants, it has been observed that they are subject to noise pickup and, also, to an offset or shift in the pH reading. It has further been discovered that the major source of error in high purity water measurements is caused by parasitic leakage currents flowing from the grounded solution through the reference electrode when said electrode is connected to a low impedance point in the electronic circuit. These leakage currents then flow through the low impedance path to the common or ground terminal of the power supply, through the power transformer, and through leakage on printed circuit cards in the system to produce, as a result, a leakage path between the circuit common and the AC power line. The instantaneous effects of the leakage currents which flow through this path are produced in direct proportion to the electrolytic resistance of the solution at the reference electrode/solution interface. The presence of parasitic AC currents in this path produces noise in the measurement and parasitic DC currents produce a shift in output, both are directly observed as errors in the pH reading. Longer term integration of DC leakage currents and electrode rectified AC currents will result in a drift of electrode output with a commensurate drift in instrument accuracy.

It is, therefore, an object of this invention to provide a potentiometric electrochemical measuring system for use with grounded low conductivity solutions, such a high purity water, which will avoid noise problems due to spurious AC currents and will avoid level shifts due to spurious DC currents.

It is a further object of this invention to provide a measuring circuit which will preclude the deleterious and permanent shifts in the output voltage of the reference electrode as a result of spurious AC and DC ground loop currents.

SUMMARY OF THE INVENTION

To carry out the present invention there is provided a potentiometric electrochemical measuring system having a control amplifier connected in circuit with an ion selective probe system so that the output of the amplifier through a counter electrode of the probe system operates to maintain the electrical characteristics of the ion selective device of the system relative to signal common potential such that the potential of the reference electrode with reference to circuit common potential, as measured by a high impedence measuring circuit, is indicative of the concentration of the selected ion.

BRIEF DESCRIPTION OF THE DRAWINGS

In the drawings, where like references refer to like elements.

DESCRIPTION OF THE PREFERRED EMBODIMENT

Figure 1:
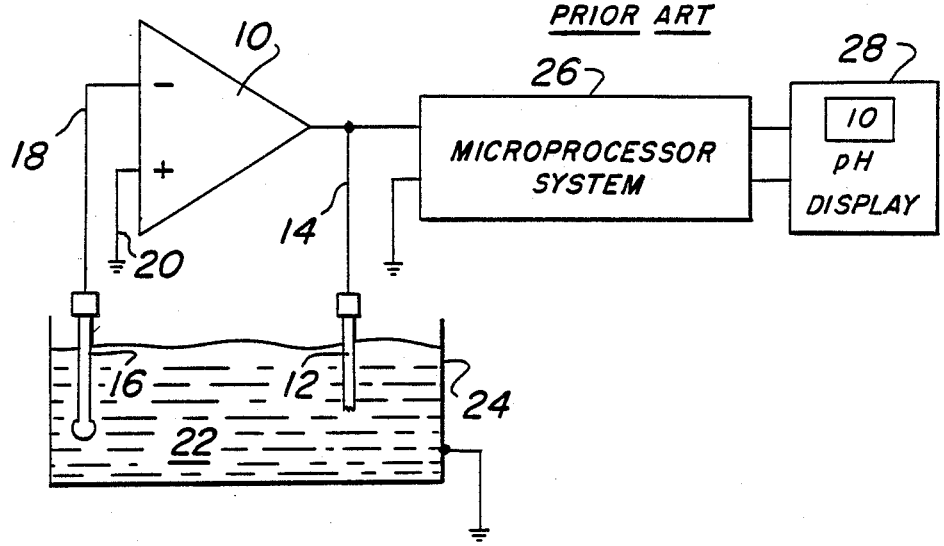
FIG. 1 is a circuit diagram of a known prior art potentiometric electrochemical measuring system for measuring pH.

FIG. 1, which illustrates the prior art systems, utilizes the control amplifier, shown as an operational amplifier 10, to drive the reference electrode 12 from the amplifier's low impedance output on line 14 so as to maintain the glass pH electrode 16, connected by line 18 to the inverting input of the amplifier, substantially at circuit common. Circuit common is the potential at the non-inverting input of the amplifier, shown as line 20. By holding the glass electrode at circuit common, the potential on line 14 at the output of the amplifier 10 is indicative of the pH of the solution 22, shown as being in a grounded container 24. A microprocessor based measuring system 26 is shown as a preferred means for processing the output of the amplifier 10 to provide an indication of the pH of the solution on the display device 28; an analog implementation can also be used.

With solutions having a conductivity below 1 micromho, for example, as is the case with high purity water, it has been found that spurious AC as well as DC currents may be present in the system and can therefore be picked up by the system. AC currents can cause noise and the DC currents can cause shifts in the reading on the display. An undesirable side effect, which is not immediately evident, is the possible deterioration of the reference cell which may result from those currents. In view of these problems, it is highly desirable to avoid such spurious currents in the reference electrode and to find a way to keep them from interfering with the measuring system. Preventing the spurious currents by enhancing power supply isolation is both difficult and costly.

It has been found that the leakage currents, per se, are not the problem, but their flow into the reference electrode is the source of the effects noted. It is desirable, therefore, to connect the reference electrode to a low leakage, high impedance system in order to inhibit current flow. This has been accomplished by inserting an additional metal electrode, such as electrode 30, into the solution being measured in order to channel the spurious currents through that electrode rather than through the reference electrode. This additional electrode may be properly called a counter electrode. Thus, in FIG. 2 a metal wire is shown as counter electrode 30, and it is connected to the output of the amplifier 10, where the reference electrode was connected in the prior art systems. The reference electrode 12 is then connected to the measuring circuit, which consists of the microprocessor based measuring system 26 and the display unit 28. In order to further prevent the flow of spurious currents in the reference electrode, as was mentioned above, it is necessary to connect it to the measuring system through a high impedance circuit, such as a the buffer amplifier 32. A further advantage accrues from improved reference electrode stability because the reduction of spurious AC and DC currents reduces electrochemical changes in the reference electrode.

Figure 2:
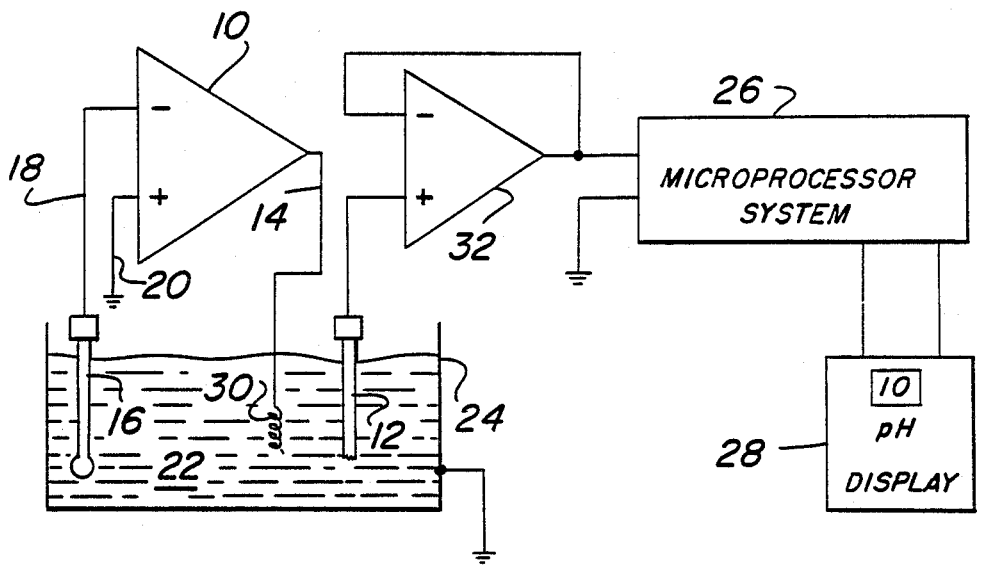
FIG. 2 is a circuit diagram of a pH measuring system which utilizes the invention with a glass electrode system.

In the circuit of FIG. 2, the counter electrode is driven by the output of the amplifier so that the pH electrode is maintained at signal common, as occured in the prior art system of FIG. 1 with the reference electrode connected to the amplifier output. The voltage obtained at the metal counter electrode is unimportant, for it only serves to maintain the glass electrodes potential at signal common. The counter electrode may, by way of example, be a metallic electrode housing or an earth grounded pipe fitting in close proximity to the pH electrode. Because its potential is unimportant, parasitic currents in the counter electrode are of no consequence. Since the glass electrode is controlled to be at circuit common, it is only necessary to measure with a measuring circuit of high input impedance the potential of the reference electrode versus signal common in order to obtain a measure of the pH. With this circuit, it has been found that AC noise rejection has been improved, and there is virtual immunity to DC leakage currents.

Figure 3:
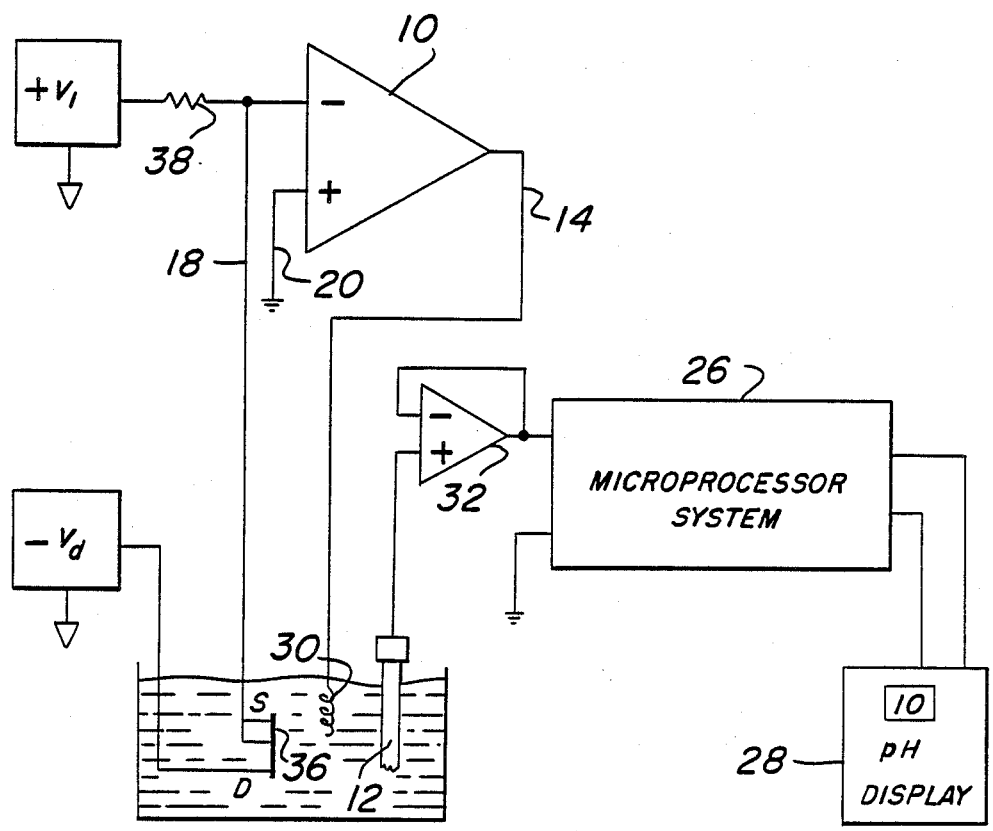
FIG. 3 is a circuit diagram of a pH measuring system which utilizes an ISFET type pH sensitive device.

The principles of this improved circuit can also be applied to ISFET probe system, as is shown in FIG. 3. In that figure a P-channel enhancement mode ISFET 36 has its source connected to the inverting input of the amplifier 10. The voltage source $-V_d$ controls the drain-source voltage at the preselected level. A source of potential is connected to the inverting input of the amplifier by way of a resistor $R_1$, shown as 38, which controls the drain current at $V_1/R_1$. As is also shown in FIG. 3, the reference electrode 12 is connected to the input of the measuring system and the output of the amplifier is connected to a counter electrode 30. The ISFET electrode system may, in one of its possible forms, be constructed as disclosed in U.S. Pat. No. 4,505,799, issued on Mar. 19, 1985 to Ronald D. Baxter, a coworker of ours.

What is claimed is:

1. An improved apparatus for measuring the concentration of a selected ion in an electrolyte solution, comprising:
   an ion selective probe system having
      an ion selective device responsive to the concentration of the selected ion in the solution,
      a reference electrode, and
      a counter electrode;
   a potential measuring device having a high impedance input connected to said reference electrode so as to measure the potential of the reference electrode with respect to circuit common; and
   a control amplifier connected to said probe system so that its output is provided through said counter electrode in magnitude and sense to maintain the electrical characteristic of said ion selective device relative to the circuit common potential such that the potential of said reference electrode, as measured by said measuring device, provides an indication of the concentration of said selected ion in said solution.

2. An apparatus as set forth in claim 1 in which said control amplifier is an operational amplifier having its inverting input connected to the ion selective device, its non-inverting input connected to circuit common, and its output connected to the counter elelctrode so that said amplifier tends to drive the potential of the ion selective device to circuit common potential.

3. Apparatus, as set forth in claim 2, in which the ion selective device is a pH glass electrode.

4. An apparatus as set forth in claim 1, in which the ion selective device is an ISFET, and said amplifier is connected to said probe system so that its output through said counter electrode is effective to maintain a constant drain-to-source voltage and drain-to-source current.

5. An apparatus for measuring pH in an electrolyte solution, comprising:
   an operational amplifier having an inverting input, a non-inverting input connected to circuit common, and an output;
   a counter electrode connected to the output of the amplifier;
   an ISFET pH responsive device having its drain connected to a voltage supply and its source connected to the inverting input of the amplifier and to a voltage supply by way of a resistor so that said amplifier drives the counter electrode to control the drain-source voltage and the drain current to be constant;
   a potential measuring circuit having a high impedance input; and
   a reference electrode connected to the high impedance input of said potential measuring circuit, whereby the potential measured is representative of the pH of the solution.

6. Apparatus, as set forth in claim 5, in which the counter electrode is a metal electrode physically mounted in close proximity to the ISFET electrode.

7. An improved apparatus for measuring the concentration of a selected ion in an electrolyte solution, comprising:
   an operational amplifier having an inverting input, a non-inverting input, and an output;
   an ion selective electrode;
   a reference electrode;
   a counter electrode;
   means for electrically connecting the ion selective electrode to the inverting input of the amplifier, connecting the counter electrode to the output of the amplifier, and connecting the non-inverting input to circuit common so that said amplifier drives said ion selective electrode to the potential of circuit common; and
   measuring means having a high impedance input for measuring the voltage level with respect to circuit common of the reference electrode as a measure of the concentration of the selected ion in the solution being measured.

8. Apparatus, as set forth in claim 7, in which the counter electrode is a metal electrode.

9. An improved apparatus for measuring the concentration of a selected ion in an electrolyte solution, comprising:
   an ion selective electrode;
   a reference electrode;
   a counter electrode; and an operational amplifier having its inverting input connected to the ion selective electrode, its non-inverting input connected to circuit common, and its output connected to the counter electrode so that said amplifier tends to drive the potential of the ion selective electrode to circuit common, whereby the potential on the reference electrode is indicative of the concentration of the selected ion.

* * * * *